US006511499B2

(12) United States Patent
Schmieding et al.

(10) Patent No.: US 6,511,499 B2
(45) Date of Patent: *Jan. 28, 2003

(54) CORKSCREW SUTURE ANCHOR

(75) Inventors: Reinhold Schmieding, Naples, FL (US); R. Donald Grafton, Naples, FL (US); Mark Brunsvold, Naples, FL (US)

(73) Assignee: Arthrex, Inc., Naples, FL (US)

( * ) Notice: Subject to any disclaimer, the term of this patent is extended or adjusted under 35 U.S.C. 154(b) by 5 days.

This patent is subject to a terminal disclaimer.

(21) Appl. No.: 09/823,988

(22) Filed: Apr. 3, 2001

(65) Prior Publication Data

US 2001/0037131 A1 Nov. 1, 2001

Related U.S. Application Data

(63) Continuation of application No. 09/588,065, filed on Jun. 5, 2000, now Pat. No. 6,214,031, which is a continuation of application No. 08/954,206, filed on Oct. 20, 1997, now Pat. No. 6,117,162, which is a continuation of application No. 08/905,393, filed on Aug. 4, 1997, now abandoned.
(60) Provisional application No. 60/023,011, filed on Aug. 5, 1996.

(51) Int. Cl.$^7$ ............................................. A61B 17/04
(52) U.S. Cl. ........................................ 606/232; 606/73
(58) Field of Search ................................. 606/232, 73

(56) References Cited

U.S. PATENT DOCUMENTS

| | | | | |
|---|---|---|---|---|
| 4,175,555 A | 11/1979 | Herbert | ........................ | 623/73 |
| 4,289,124 A | 9/1981 | Zickel | .......................... | 606/60 |
| 4,537,185 A | 8/1985 | Stednitz | ........................ | 606/73 |
| 4,632,100 A | 12/1986 | Somers et al. | ................. | 606/73 |
| 4,870,957 A | 10/1989 | Goble et al. | | |
| 4,988,351 A | 1/1991 | Paulos et al. | ................. | 606/72 |
| 5,061,181 A | 10/1991 | Niznick | ....................... | 433/174 |

(List continued on next page.)

FOREIGN PATENT DOCUMENTS

| | | |
|---|---|---|
| FR | 2588332 | 4/1987 |
| SU | 1034734 | 8/1983 |

OTHER PUBLICATIONS

"Implants for Surgery–Metal Bone Screws With Hexagonal Drive Connection, Spherical Under–surface of Head, Asymmetrical Thread–Dimensions," International Standard *ISO 5835*, 1991(E), pp. 1–10.
"Bone Screw Technical Information," Richards Manufacturing Company, Inc. Tech. Publ. 1980, pp. 1–14.
Linvatec Revo™ Cancellous Screw advertisement, 1993.

*Primary Examiner*—Gary Jackson
(74) *Attorney, Agent, or Firm*—Dickstein Shapiro Morin & Oshinsky, LLP

(57) ABSTRACT

A corkscrew suture anchor has a continuous thread spiralling around a tapering central core. At the distal end, the suture anchor terminates in a rounded point. At the proximal end of the suture anchor is an eye for receiving suture. The suture anchor has a large thread surface per turn of thread. Antibackout ridges can be formed on the front and/or back faces of the threads. A driver for the suture anchor is provided, the driver including a shaft having a central axis, a length, a distal end, and a proximal end. The shaft is provided at its distal end with an opening aligned with the central axis of the shaft, for receiving the hexagonal proximal end of the suture anchor. One or more sutures threaded through the suture eye are threaded through the hollow tubular shaft. The suture is pulled into and captured by V-shaped notches on the proximal end of the handle to hold the suture anchor in place on the distal end of the driver under the tension of the captured sutures.

16 Claims, 2 Drawing Sheets

U.S. PATENT DOCUMENTS

| | | | |
|---|---|---|---|
| 5,067,956 A | 11/1991 | Buford, III et al. | 606/73 |
| 5,100,417 A | 3/1992 | Cerier et al. | 606/139 |
| 5,102,414 A | 4/1992 | Kirsch | |
| 5,139,499 A | 8/1992 | Small et al. | |
| 5,152,790 A | 10/1992 | Rosenberg et al. | 623/13 |
| 5,156,616 A | 10/1992 | Meadows et al. | 606/232 |
| 5,180,382 A | 1/1993 | Frigg et al. | 606/65 |
| 5,242,447 A | 9/1993 | Borzone | 606/73 |
| 5,246,441 A | 9/1993 | Ross et al. | 606/53 |
| 5,364,400 A | 11/1994 | Rego, Jr. et al. | 606/72 |
| 5,370,662 A | 12/1994 | Stone et al. | 606/232 |
| 5,417,533 A | 5/1995 | Lasner | 411/426 |
| 5,443,482 A | 8/1995 | Stone et al. | 606/232 |
| 5,447,401 A | 9/1995 | Jones et al. | 411/424 |
| 5,456,685 A | 10/1995 | Huebner | 606/73 |
| 5,470,334 A | 11/1995 | Ross et al. | |
| 5,492,442 A | 2/1996 | Lasner | 411/426 |
| 5,522,843 A | 6/1996 | Zang | 606/232 |
| 5,571,139 A | 11/1996 | Jenkins, Jr. | |
| 5,573,548 A | 11/1996 | Nazre et al. | 606/232 |
| 5,607,432 A | 3/1997 | Fucci | 606/104 |
| 5,618,314 A | 4/1997 | Harwin et al. | |
| 5,626,613 A | 5/1997 | Schmieding | |
| 5,643,269 A | 7/1997 | Harle | 606/79 |
| D385,352 S | 10/1997 | Bales et al. | D24/145 |
| 5,683,401 A | 11/1997 | Schmieding et al. | 606/104 |
| 5,690,676 A | 11/1997 | DiPoto et al. | |
| 5,697,950 A | 12/1997 | Fucci et al. | 606/232 |
| 5,720,766 A | 2/1998 | Zang et al. | 606/232 |
| 5,733,307 A | 3/1998 | Dinsdale | 606/232 |
| 5,738,685 A | 4/1998 | Halm et al. | 606/61 |
| 5,743,914 A | 4/1998 | Skiba | 606/73 |
| 5,792,142 A | 8/1998 | Galitzer | |
| 5,824,011 A | 10/1998 | Stone et al. | |
| 5,827,291 A | 10/1998 | Fucci et al. | 606/104 |
| 5,851,219 A | 12/1998 | Goble et al. | |
| 6,117,162 A | 9/2000 | Schmieding et al. | 606/232 |
| 6,214,031 B1 | 4/2001 | Schmieding et al. | 606/232 |

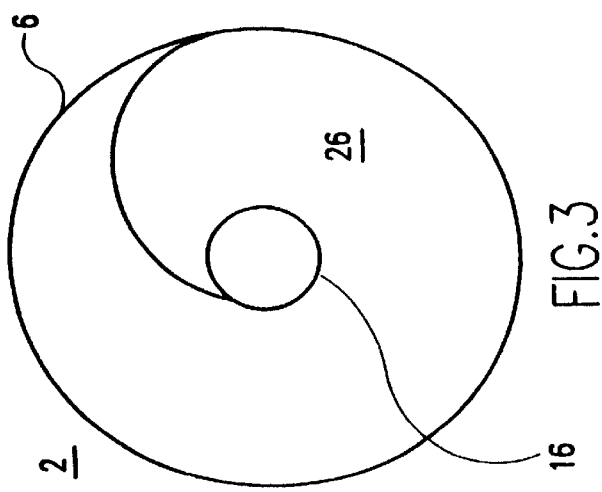
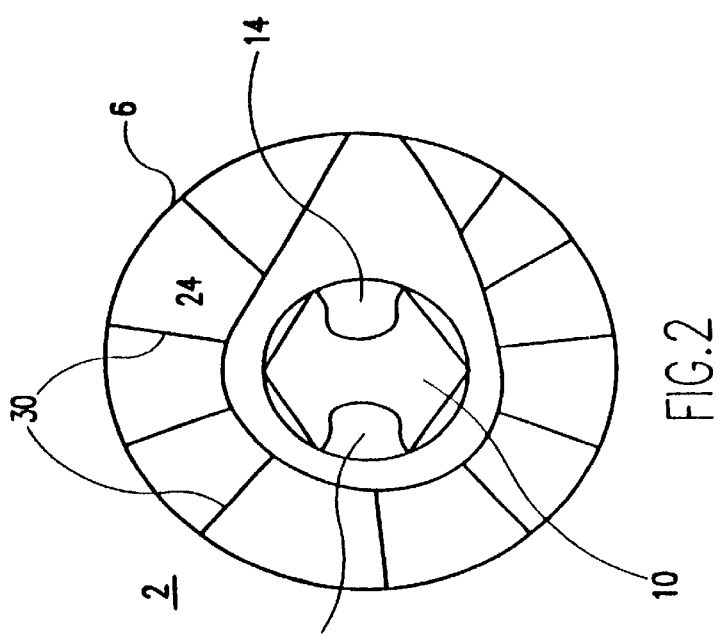
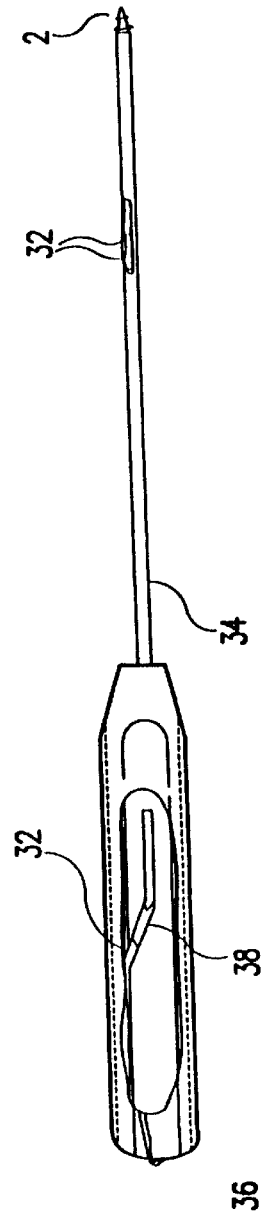

CORKSCREW SUTURE ANCHOR

This application is a continuation of U.S. Ser. No. 09/588,065, filed Jun. 5, 2000, now U.S. Pat. No. 6,214,031, which is a continuation of U.S. Ser. No. 08/954,206, filed Oct. 20, 1997, now U.S. Pat. No. 6,117,162, which is a continuation of Ser. No. 08/905,393, filed Aug. 4, 1997, now abandoned, and claims the benefit of U.S. Provisional Application No. 60/023,011, filed Aug. 5, 1996.

BACKGROUND OF THE INVENTION

1. Field of the Invention

The present invention relates to an apparatus and method for anchoring surgical suture to bone. More specifically, the present invention relates to arthroscopic apparatus and methods for anchoring suture to cancellous bone using a suture anchor having an auger-like configuration.

2. Description of the Related Art

When soft tissue tears away from bone, reattachment becomes necessary. Various devices, including sutures alone, screws, staples, wedges, and plugs have been used to secure soft tissue to bone. Recently, various types of threaded suture anchors have been developed for this purpose.

Suture anchors have been developed that are designed to be inserted into a pre-drilled hole. Other suture anchors are self-tapping. Self-tapping screws are shown, for example, in U.S. Pat. No. 4,632,100, which discloses a cylindrical suture anchor. The suture anchor of the '100 patent includes a drill bit at a leading end for boring a hole in a bone, followed by a flight of threads spaced from the drill bit for securing the anchor into the hole created by the drill bit. U.S. Pat. No. 5,370,662 discloses a self-tapping suture anchor having a flight of threads around a solid body. U.S. Pat. No. 5,156,616 discloses a similar suture anchor having an axial opening for holding a knotted piece of suture.

All of the above-noted suture anchors rely on a flight of threads disposed on the outer surface of a shank to secure the anchor to the bone. They all provide a relatively easy method of suture fixation in hard, cortical bone.

Recent studies indicate, however, that the above-noted suture anchors may have problems related to inadequate "pull-out" strength. This is true especially in softer bone sites, such as cancellous bone, or in bone tissue that has become compromised, such as in osteoporotic bone sites. The structure of cancellous, or cancellated, bone is lattice-like, or spongy. Osteoporotic bone is the result of a condition that reduces the quantity of bone or atrophies skeletal tissue, causing a porous condition of the bones. These bone types may present a limited range of specific fixation points that are available to the surgeon.

Also, certain known suture anchors also have a tendency to "back out" of the implantation site. Moreover, substantial bone loss is incurred simply upon installation of the above-described prior art suture anchors. This problem is acute particularly during procedures that require removal or relocation of suture anchors.

Accordingly, a need exists for a suture anchor that can be secured easily and effectively, especially in softer types of bone. A need also exists for a suture anchor that displaces a minimum amount of bone upon insertion. In addition, a need exists for a suture anchor having exceptional pull-out strength, especially in soft bone. A need also exists for a suture anchor that is averse to "backing out" of the insertion site.

SUMMARY OF THE INVENTION

The suture anchor of the present invention overcomes disadvantages of the prior art, such as those noted above, and achieves the foregoing objectives by providing a corkscrew suture anchor having preferably a single thread spiralling helically around a central body.

The corkscrew suture anchor has a central body, a distal end, and a proximal end. The central body preferably tapers from the proximal end to terminate in a point at the distal end. The distal point preferably is rounded to avoid possible breakage sometimes encountered when using a sharp point. The point is approached by a concave cone having a taper more pronounced than that of the central body.

The proximal end of the corkscrew suture anchor body has a hex drive head incorporating a slotted suture eye for receiving one or more pieces of suture. At the junction between the hex drive head and the central body, the circumference of the central body advantageously is larger than the outer circumferential dimension of the hex drive head. Accordingly, the enlarged body adjacent the hex drive head forms a hole sufficient to accommodate a hex driver disposed over the hex drive head. The hex driver is described more fully below. This allows the suture anchor to be at least partially countersunk below the surface of the bone upon installation by preventing impingement of the distal end of the hex driver on the bone surface.

Advantageously, the threads of the suture anchor of the present invention provide an increased percentage of thread surface area for each turn of the screw, as compared with known suture anchors, thus providing increased pull-out strength, and a decreased tendency for back-out. The increase in the surface area of the thread is achieved in part by increasing the ratio of the outer diameter of the threads to the inner diameter of the threads. Preferably, the ratio is between 2.25 and 2.75. Most preferably, the ratio of the outer diameter to the inner diameter is 2.5.

In addition, the suture anchor has a higher thread pitch than prior art screws, thus increasing the area of thread for each turn of the screw, which also leads to greater pull-out strength. Significantly, due to the increased pitch, fewer turns of the corkscrew screw thread are required to advance the suture anchor into position. Accordingly, the suture anchor is easy to install, and displaces less tissue material upon insertion than known suture anchors.

The pull-out strength and minimal tissue damage are enhanced by the relatively compressed cross-sectional aspect of the thread, particularly in relation to the broad axial faces of the threads. The distal and proximal faces of the threads preferably form a square or rounded break edge at the outer diameter of the thread. In addition, the thickness of the thread increases proximally, such that at least the most proximal flight is thicker than each of the more distal flights.

Increased back-out resistance is enhanced by surface features, such as radial ridges, on the top and/or bottom faces of the screw threads. The surface features augment the engagement between the thread surfaces and the surrounding tissue once the suture anchor is installed.

The present invention also provides a suture anchor and driver assembly for driving the corkscrew suture anchor into bone. The driver is formed of a cannulated tube secured to a cannulated handle. A hexagonal socket formed on the distal end of the tube holds the suture anchor for rotation and installation into the bone. The outer diameter of the tube is equal to or less than the outer diameter of the proximal end of the suture anchor's central body.

The driver is provided with a cleat on the side of the handle. Consequently, suture threaded through the cannulated driver can be wrapped around the cleat and fixed for shipping in a slot in the cleat using adhesive foam. One or more sutures, threaded through the suture anchor eye and up through the cannulated driver, can be pulled and secured around the cleat, whereby the suture is pinched under tension. Advantageously, the tensioned suture helps to hold the suture anchor in place at the distal tip of the driver. The suture anchor and driver assembly can be shipped, pre-loaded with suture, as a sterile, surgery-ready unit.

The present invention also provides a method of anchoring suture in bone using the suture anchor of the present invention. The method includes threading suture through the suture eye on the proximal end of the suture anchor. The driver is then turned to advance the suture anchor into the bone.

The anchors of the present invention can be used for arthroscopic procedures. Advantageously, the suture anchor can be installed using a hollow, cannulated grasper as described in U.S. Pat. No. 5,466,243 to Schmieding, the disclosure of which is incorporated herein by reference. The anchors also are advantageous for open and mini-open surgical procedures, such as open rotator cuff repair, as described in U.S. Pat. No. 5,575,801 to Habermeyer et al.

Other features and advantages of the present invention will become apparent from the following description of the invention, which refers to the accompanying drawings.

BRIEF DESCRIPTION OF THE DRAWINGS

FIG. 2 is a proximal end view of the corkscrew suture anchor if FIG. 1.

FIG. 3 is a distal end view of the suture anchor of FIG. 1.

FIG. 4 is a side view of a suture anchor assembly including a suture anchor, threaded with suture, and a driver according to the present invention.

DETAILED DESCRIPTION OF THE PREFERRED EMBODIMENTS

Figure 1:
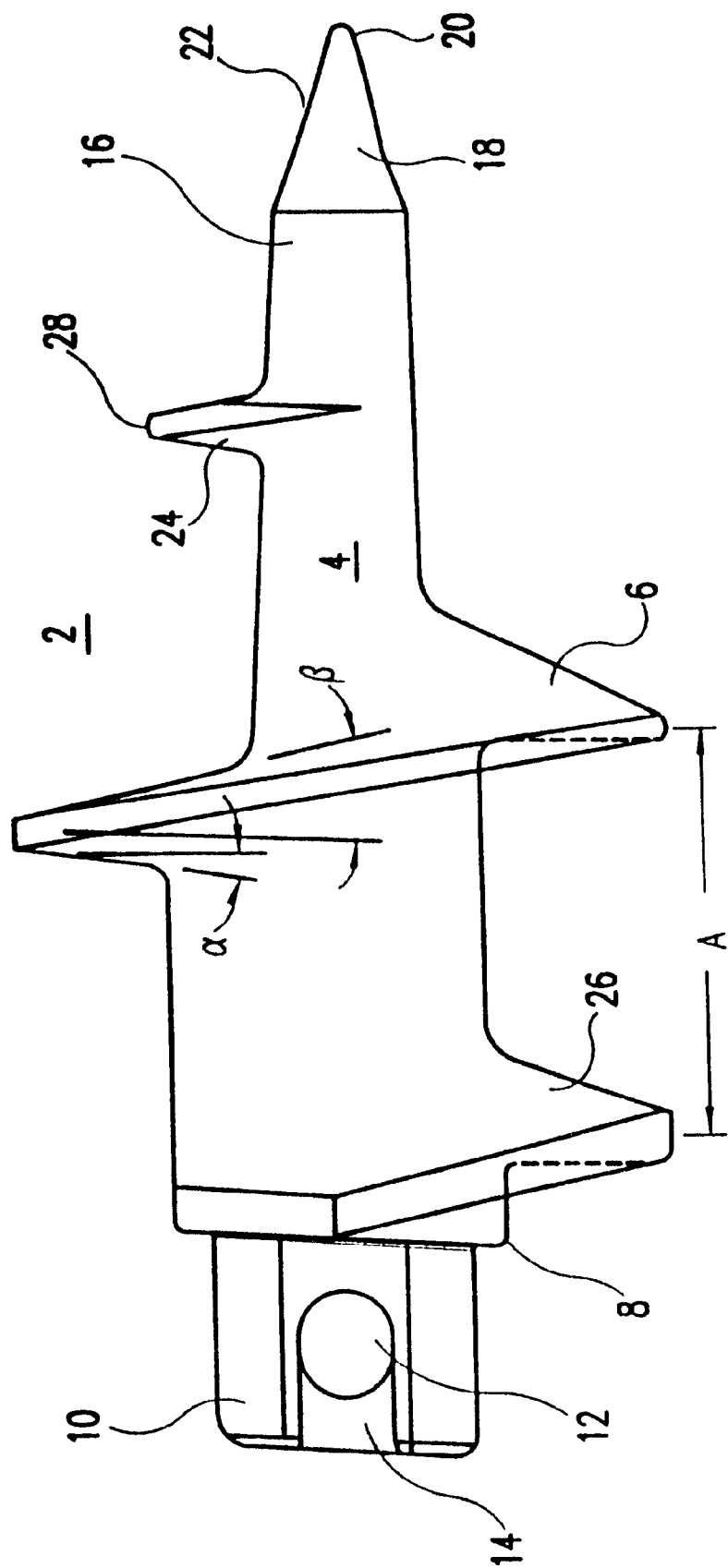
FIG. 1 is a side view of a corkscrew suture anchor according to the present invention.

Referring to FIG. 1, the suture anchor 2 of the present invention includes a body 4 provided in the shape of a tapered cylinder. A continuous thread 6 wraps around body 4 in a clockwise direction, as shown.

Suture anchor 2 is provided at a proximal end S of body 4 with hexagonal drive head 10 having a suture eye 12. The suture eye 12 preferably is in the form of an oval aperture in the drive head for holding at least one, and preferably two or more pieces of braided suture. Channels 14, also shown in FIG. 2, are formed along either side of the drive head 10 to accommodate the suture, such as when the suture anchor is held in a suture anchor driver, set forth more frilly below.

A tip 18 is provided. Tip 18 terminates in a rounded point 20, which is approached by a concave, conically tapered surface 22. Conical taper 22 begins at the distal end of the screw thread, and features an angle of taper deeper than the taper of body 4.

The body preferably is formed of a biocompatible material such as stainless steel or titanium alloy. The central core preferably is circular in cross-section, and tapers from a maximum diameter near proximal end 8 to a minimum diameter toward distal end 14.

Corkscrew thread 6 has a proximal face 24, a distal face 26 and a break edge 28. Referring to FIG. 2, suture anchor 2 is shown from the proximal end. Radial ridge lines 30 are shown on proximal face 24 of corkscrew thread 6.

The major, outside diameter of the suture anchor thread of the present invention preferably is about 2.5 times the minor, inner diameter of the thread, or the minor diameter of the body toward distal end 16. Accordingly, on a 5 mm. diameter suture anchor, for example, where central core 4 is approximately 2 mm. in diameter, the outer diameter of the thread is 5 mm.

Preferably, between two and three flights or turns of thread 6 are provided along body 4, between proximal end 8 and distal end 16. The thickness of the thread increases proximally, such that at least the outer edge of the most proximal flight is thicker than the edge of each of the more distal flights, as shown in FIG. 1. Adjacent sections of each flight are separated by a gap that is determined by the number of turns per inch of the suture anchor thread. For example, a 5 mm. suture anchor preferably has 6 turns per inch, while a 3.5 mm. suture anchor preferably has about 9. Accordingly, on a 5 mm or 6.5 mm suture anchor, the pitch distance A from flight to flight is 0.167 inches. On a 3.5 mm suture anchor, pitch distance A typically is 0.118 inches.

Referring again to FIG. 1, proximal thread surface 24 forms a 10 angle with an axial perpendicular to the central axis of the body 4, in the case of a 3.5 or 5.0 mm suture anchor, and a 5 angle in a 6.5 mm suture anchor. Distal thread surface 26 preferably forms a 20 angle β with an axial perpendicular to the central axis of the body 4, in the case of a 3.5 or 5.0 mm suture anchor, and a 15 angle β in a 6.5 mm suture anchor, as shown in Table I, as follows:

TABLE I

Suture Anchor Dimensions and Features

| | Size | 3.5 | 5.0 | 6.0 |
|---|---|---|---|---|
| Thread | No. | 2.5 | 2 | 2 |
| Flights | Pitch (A) (mm.) | 3.0 | 4.24 | 4.24 |
| Diameter | Major | 3.5 | 5.0 | 6.0 |
| (mm) | Minor | 1.22 | 1.40 | 1.40 |
| Thread | α | 10 | 10 | 5 |
| Angle (°) | β | 20 | 20 | 15 |

FIG. 4 shows suture anchor 2 threaded with two pieces of suture 32 and held on a cannulated suture anchor driver 34. The suture is wrapped around cleat 36. Tension on the suture aids in retaining the suture anchor in the distal end of the driver. The suture is held in place in slot 38 using a foam adhesive, for example, during shipping. The assembly is provided as a sterile unit ready for surgical application.

Table II shows the results of various pullout tests performed with suture anchors according to the present invention, as follows:

TABLE II

Pull-out strength of corkscrew suture anchors

| | 5.0 mm anchor | | 6.5 mm anchor |
|---|---|---|---|
| Test No. | 20 lb. bone block | 30 lb. bone block | 20 lb bone block |
| 1 | N/A | 112.2 (wire break) | 98.4 (wire break) |
| 2 | 116.1 (pulled out) | 106.9 (wire break) | 119.2 (wire break) |

TABLE II-continued

Pull-out strength of corkscrew suture anchors

|  | 5.0 mm anchor | | 6.5 mm anchor |
| --- | --- | --- | --- |
| Test No. | 20 lb. bone block | 30 lb. bone block | 20 lb bone block |
| 3 | 95.4 (pulled out) | 111.5 (wire break) | 125.1 (wire break) |
| 4 | 104.9 (pulled out) | 99.6 (wire break) | 99.7 (slot break) |
| 5 | 125.1 (pulled out) | 84.7 (wire break) | 125.2 (wire break) |
| Avg. | 110.375 | 103.0 | 113.52 |
| St. dev. | 13.0 | 11.4 | 13.4 |

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A suture anchor for securing suture to soft bone, comprising:
    a central body having a central axis, a distal end and a proximal end, the central body tapering in diameter along a major portion thereof from a maximum diameter near the proximal end to a minimum diameter toward the distal end;
    a drive head formed on the proximal end of the central body;
    an eyelet for receiving at least one strand of suture formed on the proximal end of the central body;
    a tip formed on the distal end of the central body; and
    a continuous thread disposed in a spiral around the central body, the thread having an outer edge having a thickness, the thickness of the outer edge of the thread increasing proximally along a portion of the thread;
    wherein the continuous thread extends at least along the major portion of the central body; and
    wherein the outer diameter of the thread is at least twice the inner diameter of the thread along a portion of the thread.

2. The suture anchor of claim 1, further comprising channels for suture on the drive head.

3. The suture anchor of claim 1, further comprising two lengths of suture attached to the suture anchor.

4. The suture anchor of claim 1, wherein the drive head is hexagonal.

5. An assembly of a suture anchor for securing suture to soft bone, and a driver for driving the suture anchor into said soft bone, the assembly comprising:
    a driver comprising a tubular shaft having a distal end and a proximal end, and a handle disposed on the proximal end of the shaft;
    a suture anchor inserted into the distal end of the driver, the suture anchor comprising:
        a central body having a central axis, a distal end and a proximal end, the central body having a diameter along a major portion thereof tapering from a maximum diameter to a minimum diameter toward the distal end, and a tip portion formed on the distal end of the central body, the tip portion terminating in a point;
        a drive head disposed on the proximal end of the central body, the drive head having an eyelet for suture; and
        a continuous thread disposed in a spiral around the central body, the thread having a thickness and an outer diameter, the thickness of the thread increasing proximally along a portion of the length of the thread, the outer diameter of the thread being at least twice the inner diameter of the thread along a portion of the thread; and
    at least one strand of suture passed through an eyelet in the suture anchor, through the tubular shaft, through at least a portion of the handle, and exiting the handle, the suture being secured to the handle so as to retain the suture anchor on the distal end of the tubular shaft.

6. The suture anchor and driver assembly of claim 5, further comprising a cleat for holding the suture on an outer surface of the handle.

7. The suture anchor and driver assembly of claim 6, wherein the cleat includes a slot for holding the suture.

8. A suture anchor for securing suture to soft bone, comprising:
    a central body having a central axis, a distal end and a proximal end, the central body tapering in diameter along a major portion thereof from a maximum diameter near the proximal end to a minimum diameter toward the distal end;
    a tip portion formed on the distal end of the central body, the tip portion having a conical shape and tapering from the minimum diameter to a point, the tip portion having a taper that is greater than the taper of the major portion of the central body;
    a drive head formed on the proximal end of the central body;
    an eyelet for receiving at least one strand of suture formed on the proximal end of the central body; and
    a continuous thread disposed in a spiral around the central body;
    wherein the continuous thread extends at least along the major portion of the central body; and
    wherein the outer diameter of the thread is at least twice the inner diameter of the thread along a portion of the thread.

9. The suture anchor of claim 8, further comprising channels for suture on the drive head.

10. The suture anchor of claim 8, further comprising two lengths of suture attached to the suture anchor.

11. The suture anchor of claim 8, wherein the drive head is hexagonal.

12. A suture anchor for securing tissue to soft bone, comprising:
    a central body having a central axis, a distal end and a proximal end, the central body tapering in diameter along a portion thereof from a maximum diameter near the proximal end to a minimum diameter in a direction toward the distal end;
    a tip portion formed on the distal end of the central body, the tip portion terminating in a point;
    a drive head formed on the proximal end of the central body;
    an eyelet for receiving at least one strand of suture formed on the drive head; and a continuous thread disposed in a spiral around the central body, said continuous thread extending at least along the tapered portion of the central body, said continuous thread having an inner diameter and an outer diameter; wherein the outer diameter of the thread is at least twice the inner diameter along a portion of the thread.

13. The suture anchor of claim 12, wherein the continuous thread has a thickness, the thickness of the thread increasing proximally along a portion of the thread.

14. The suture anchor of claim 12, further comprising channels for suture on the drive head.

15. The suture anchor of claim 12, further comprising two lengths of suture attached to the suture anchor.

16. The suture anchor of claim 12, wherein the drive head is hexagonal.

* * * * *